United States Patent [19]

Stripf et al.

[11] Patent Number: 5,497,661

[45] Date of Patent: Mar. 12, 1996

[54] METHOD OF MEASURING THE DELAY OF ULTRASOUND IN THE PULSE REFLECTION METHOD

[75] Inventors: Helmut Stripf, Eggenstein-Leopoldshafen; Thomas Kühner; Armin Herth, both of Karlsruhe, all of Germany

[73] Assignees: Kernforschungszentrum Karlsruhe GmbH, Karlsruhe; Pipetronix GmbH, Stutensee, Germany

[21] Appl. No.: 927,319

[22] PCT Filed: Dec. 12, 1991

[86] PCT No.: PCT/DE91/00964

§ 371 Date: Sep. 30, 1992

§ 102(e) Date: Sep. 30, 1992

[87] PCT Pub. No.: WO92/10746

PCT Pub. Date: Jun. 25, 1992

[30] Foreign Application Priority Data

Dec. 15, 1990 [DE] Germany ................. 40 40 190.1

[51] Int. Cl.⁶ .................................................. G01N 29/04
[52] U.S. Cl. .................................................. 73/611; 73/616
[58] Field of Search ................. 73/609, 611, 616, 73/622, 629

[56] References Cited

U.S. PATENT DOCUMENTS

| | | | |
|---|---|---|---|
| 3,583,211 | 6/1971 | Brech et al. | 73/67.5 |
| 4,210,904 | 7/1980 | Renzel | 364/507 |
| 4,470,304 | 9/1984 | Nusbickel | 73/611 |
| 4,513,621 | 4/1985 | Renzel | 73/611 |
| 4,517,152 | 5/1985 | Pieper | 73/611 |
| 4,665,751 | 5/1987 | Hüschelrat | 73/597 |
| 4,909,091 | 3/1990 | Ellmann et al. | 73/866.5 |
| 4,953,405 | 9/1990 | Hara et al. | 73/602 |

FOREIGN PATENT DOCUMENTS

| | | |
|---|---|---|
| 0361890 | 4/1990 | European Pat. Off. |
| 2933070C2 | 6/1982 | Germany . |
| 3108545C2 | 12/1982 | Germany . |
| 3435989C2 | 3/1987 | Germany . |
| 3822699A1 | 1/1990 | Germany . |
| 8904497 | 5/1989 | WIPO . |

OTHER PUBLICATIONS

Hillger, "Eln Neues Verfahren Zur Spitzenwertmessung Von Ultraschall–Prüflmpulsen", *messen prüfen automatisieren*, Dec. 1987, vol. 12, pp. 718–722.

Ottes, et al., "Korroslon frühzeitig erkennen", *Elektronik*, Dec., 1988, vol. 26, pp. 66–70.

Young, R. S. et al, "Digitally Controlled Ultrasonics For Testing Steel onLine", *Non–Destructive Testing* (Jun. 1976) pp. 131–135.

*Primary Examiner*—Hezron E. Williams
*Assistant Examiner*—Christine K. Oda
*Attorney, Agent, or Firm*—Spencer, Frank & Schneider

[57] ABSTRACT

A delay time measurement method for ultrasound of the type wherein a testing head transmits an excitation pulse that is as close as possible to the shape of a shock wave and traverses a pretravel path until it reaches the object to be examined which has a front wall and a rear wall, with at least one reflected pulse being generated at its front wall as well as at its rear wall. To improve the above-mentioned type method so that delay time measurements for thickness determinations and abnormalities can be performed reliably even on rough surfaces and if reflected pulses are missing or falsified, a time window is determined for the recording of reflected pulses that follow the excitation pulse, within which window all successive reflected pulses are digitized. Then the reflected pulses that lie within the time window are digitally filtered and parametrized, and the filtered and parametrized reflected pulses are fed to a computer unit and are evaluated on the basis of variable criteria using a predetermined algorithm.

4 Claims, 8 Drawing Sheets

METHOD OF MEASURING THE DELAY OF ULTRASOUND IN THE PULSE REFLECTION METHOD

The invention relates to a method for measuring the delay of ultrasound in the pulse reflection method wherein at least one excitation pulse that is as close as possible to the shape of a shock wave is emitted by a testing head and traverses a pretravel path until it reaches an object to be examined which has a front wall and a rear wall, with at least one reflected pulse being generated at its front wall as well as at its rear wall, and wherein the reflected pulses are detected by at least one ultrasound detector and are amplified by analog signal matching.

To determine the remaining wall thickness of pipelines, a delay measuring method using ultrasound operating according to the pulse reflection principle is employed in a corrosion testing scraper.

The ultrasound pulse generated at the testing head by the transmitted pulse passes through the oil, is partially reflected at the interior wall of the pipe and returns to the testing head. The remaining sonic energy penetrates into the pipe wall, is reflected to a major portion at the exterior wall of the pipe and also returns to the testing head. Depending on the attenuation of the sound, there will be multiple reflections within the pipe wall.

The determination of the delay times is effected by means of clocked counters which are started and stopped by the echo pulse sequences when predetermined thresholds are exceeded. The pretravel path results from the time delay between the transmitted pulse and the echo from the front wall; the wall thickness results from the time delay between the front wall echo and the first rear wall echo. The subsequent rear wall echoes remain unconsidered.

If the surfaces are rough, the echo pattern is an image of the surface structure covered by the sensor. Instead of a single echo pulse (as from a smooth surface), the sensor receives a pulse sequence. The echo pattern is broadened. The broadening over time is a function of the speed of sound in the medium; it is thus different at the rear wall than at the front wall of the pipe. Due to these laws, it may happen in connection with rough walls that, as a function of the wall thickness, the echo patterns from the front wall and from the rear wall blend together.

DE 3,638,936.A1 corresponding to U.S. Pat. No. 4,909,091 discloses a method of the above-mentioned type in which a rough surface either provides a false measurement of the time delay or no time delay at all for a determination of the wall thickness.

Additionally, DE 3,822,699 discloses a method in which an unequivocal time delay measurement is possible with the aid of a measurement blocking period and a triggering threshold that changes over time for the rear wall echo. However, this method fails on rough surfaces if the first front wall reflex is lower than the second or if the widening of the pulse sequence over time is longer than the time duration of the changing triggering threshold (for example, if the wall thickness increases in a pipe segment).

It is the object of the invention to improve a method of the above-mentioned type so that delay measurements for a determination of thicknesses and abnormalities can be performed reliably even on rough surfaces and also if reflected pulses are missing or the pulse reflections are falsified.

SUMMARY OF THE INVENTION

The above object is accomplished according to the present invention by a delay time measuring method for ultrasound employing the pulse reflection method, wherein at least one excitation pulse that is as close as possible to the shape of a shock wave is emitted by a testing head and traverses a pretravel path until it reaches an object to be examined which has a front wall and a rear wall, with at least one reflected pulse being generated at each of its front wall and its rear wall, and wherein the reflected pulses or echoes are detected by at least one ultrasound detector and are amplified by means of analog signal matching; with the method being characterized in that (a) a time window is set for recording the reflected pulses following the excitation pulse, within which window the front wall echo and at least two rear wall echoes lie; then (b) the reflected pulses lying within the time window are digitally filtered and parametrized, wherein for each reflected pulse the time and amplitude are detected for the maximum and for when a digital threshold value is exceeded or fallen short of; whereupon (c) the times and amplitudes of the filtered and parametrized reflected pulses are fed to a computer unit, wherein the pulses, seen over time, are checked from back to front, and an echo pulse which is then relevant is stored when its amplitude is greater or nearly identical to those pulses stored most recently, and finally (d) the lead time and the wall thickness delay time of the object are determined and stored when the distance in time between the entrance echo and the first rear wall echo coincides with the distance between the first and second rear wall echoes within a tolerance band; otherwise, the times and amplitudes of all filtered and parametrized reflected pulses belonging to one excitation pulse are stored.

Further advantageous features of the method according to the invention are likewise disclosed and include, for example, adapting the time window in a self-learning manner to the signal pattern, and intermediately storing the data in a fast memory before subjecting the data to filtering if the digitalization employs high sampling rates.

BRIEF DESCRIPTION OF THE DRAWINGS

The invention will be described below in greater detail with reference to an embodiment thereof and to the drawing figures. The following is a brief description of the drawings.

DETAILED DESCRIPTION OF THE PREFERRED EMBODIMENTS

Figure 1:
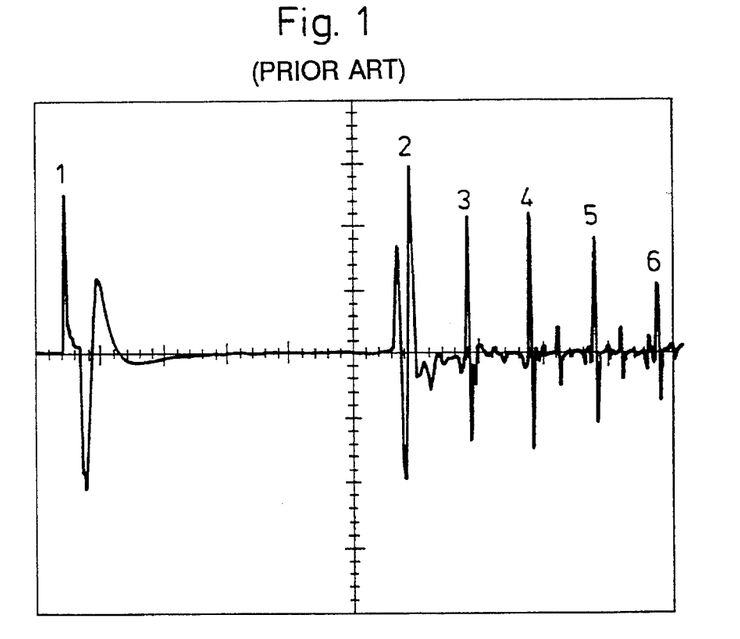
FIG. 1 depicts an ultrasound echo pattern.

In DE 3,638,936.A1, the delay is determined with the aid of clocked counters which are started and stopped by echo pulse sequences that exceed predetermined thresholds. The pretravel path results from the time delay between the transmitted pulse 1 and the front wall echo 2, the wall thickness results from the time delay between the front wall echo 2 and the first rear wall echo 3. The subsequent rear wall echoes 4, 5 and 6 remain unconsidered (FIG. 1).

As demonstrated by previous measurements, these methods often lead to erroneous interpretations in the determination of wall thicknesses although the actual signal pattern does contain information that could permit a conclusion as to the correct wall thickness.

An improvement in the echo pattern evaluation can consequently be realized in that the entire signal pattern and the subsequent pulses generated by multiple reflections are utilized for a determination of the wall thickness.

This can only be realized in that the relevant values of the pulse sequence are fed into a microprocessor system which uses them to determine the value for the wall thickness and checks it for accuracy.

The insufficient evaluation of the echo signals with the aid of the conventional delay measuring methods leads to missing or false wall thickness values. Various error categories are listed below. In each case proposed solutions in conjunction with the digitalization of the echo signal are indicated. The respective figures show an echo pattern 7, a measuring gate 8 for wall thickness measurements, and a measurement blocking aperture 9.

Figure 2:
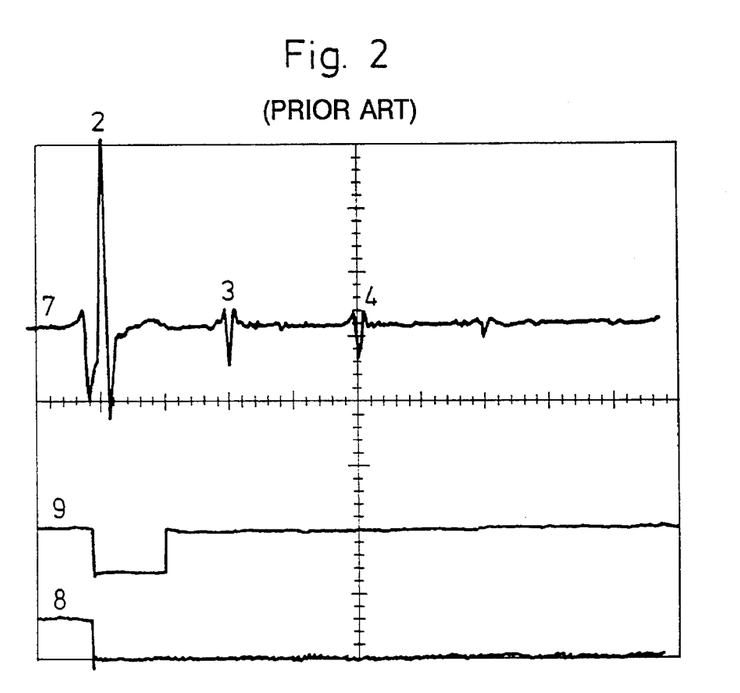
FIGS. 2, 3 and 4 depict error situations in the conventional delay measurements.

The rear wall echoes shown in FIG. 2 are too weak. Rear wall echo signal 3, 4 is so strongly attenuated by interferences or scattering that its amplitude remains below the triggering threshold. Wall thickness measuring gate 8 is consequently not closed and no measuring value is available for the wall thickness. The triggering threshold lies at about 0.8 V. A reduction of this threshold may lead to erroneous measurements due to interfering influences (crosstalk). An increase in sensitivity (with the same signal to noise ratio) can be realized by rectification and digital integration.

Figure 3:
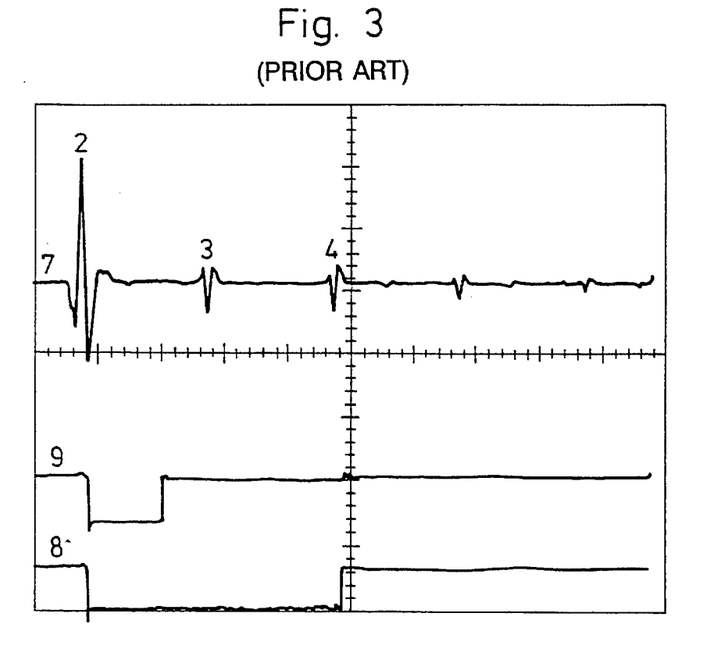

FIG. 3 shows triggering by the second instead of the first rear wall echo. Due to interferences or scattering, the amplitude of the second rear wall echo 4 may be greater than the amplitude of the first rear wall echo 3. This may lead to the counter being triggered by the second rear wall echo 4, thus the measuring result 8 indicates double the delay time. This error can be eliminated by way of plausibility monitoring and by an echo pattern evaluation that also considers the second outer wall pulse.

Figure 4:
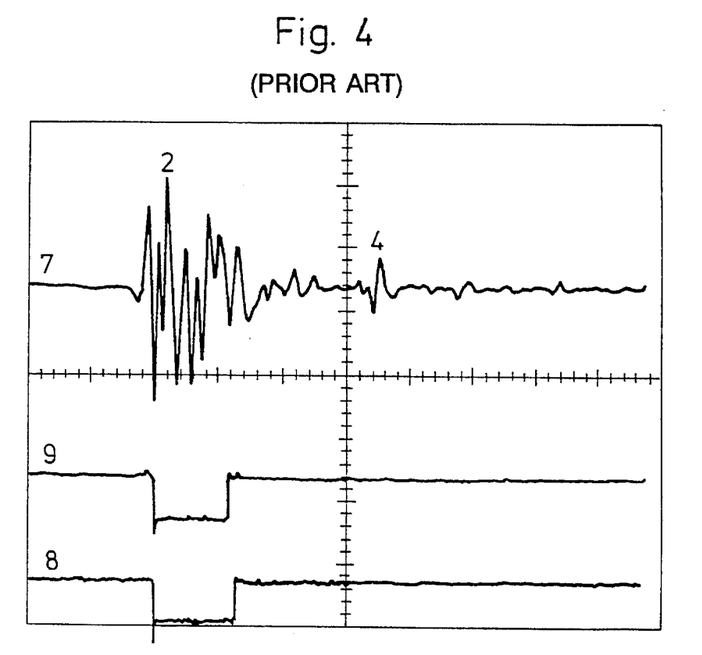

FIG. 4 shows the yield of measuring values in the range of small wall thicknesses or deep corrosion. A rough surface on the front wall leads to broadening of the front wall echo pulse 2. Instead of only one pulse, a train of echoes is received. If the wall thicknesses are small (6 mm and less) this may cause the echo patterns from the front and rear walls to blend together. To avoid erroneous measurements, the closing of the measuring gate for wall thickness measurements is prevented for a measurement blocking period 9. This aperture is set to about 1.7 µs, which corresponds to a wall thickness of 6 mm. Smaller wall thicknesses can thus not be detected. Rather, it may happen that directly after the expiration of the measurement blocking period 9, the broadened echo signal from a rough surface still lies above the triggering threshold and thus stops the counter. This then leads to a detection of the measurement blocking period as a measure for the wall thickness 8.

In order to be able to measure corrosions deeper than 6 mm, and to be able to test pipes having smaller wall thicknesses, it is necessary to evaluate the envelope of the echo pattern and to include the second and further rear wall echoes.

During the test run, the ultrasound echo received by the detector may be attenuated by various influences, for example:

A deformation of the sensor carrier or a deformation of the conduit wall may bring about that individual testing heads emit sound at an angle that deviates from the perpendicular to the wall. The result is an attenuation of the received echo signal that is a function of the deviation.

In longer oil pipelines it may happen that the surface of the ultrasonic sensors is covered by solidified oil. This soiling causes the ultrasound pulses to be attenuated. As a consequence, beginning at a certain degree of soiling, the preset triggering thresholds for the delay time measurement can no longer be exceeded; no measurement can then be taken.

A preset high pulse amplification cannot be effected because with too much basic amplification the pulses are broadened too much and this leads to erroneous delay time determinations.

Only by following with an individual amplification that is a function of the degree of attenuation, is it possible to measure the delay time in such cases.

Thus an improvement of the evaluation can be realized by digitalization of the echo signal with subsequent on-line evaluation with the aid of a suitable microprocessor system.

For this purpose, the echo signal must initially be sampled, digitized and stored in an intermediate memory. Then the pulses are sorted with the aid of a fast hardware system and their amplitude and time association are fed to the evaluation computer.

Figure 5:
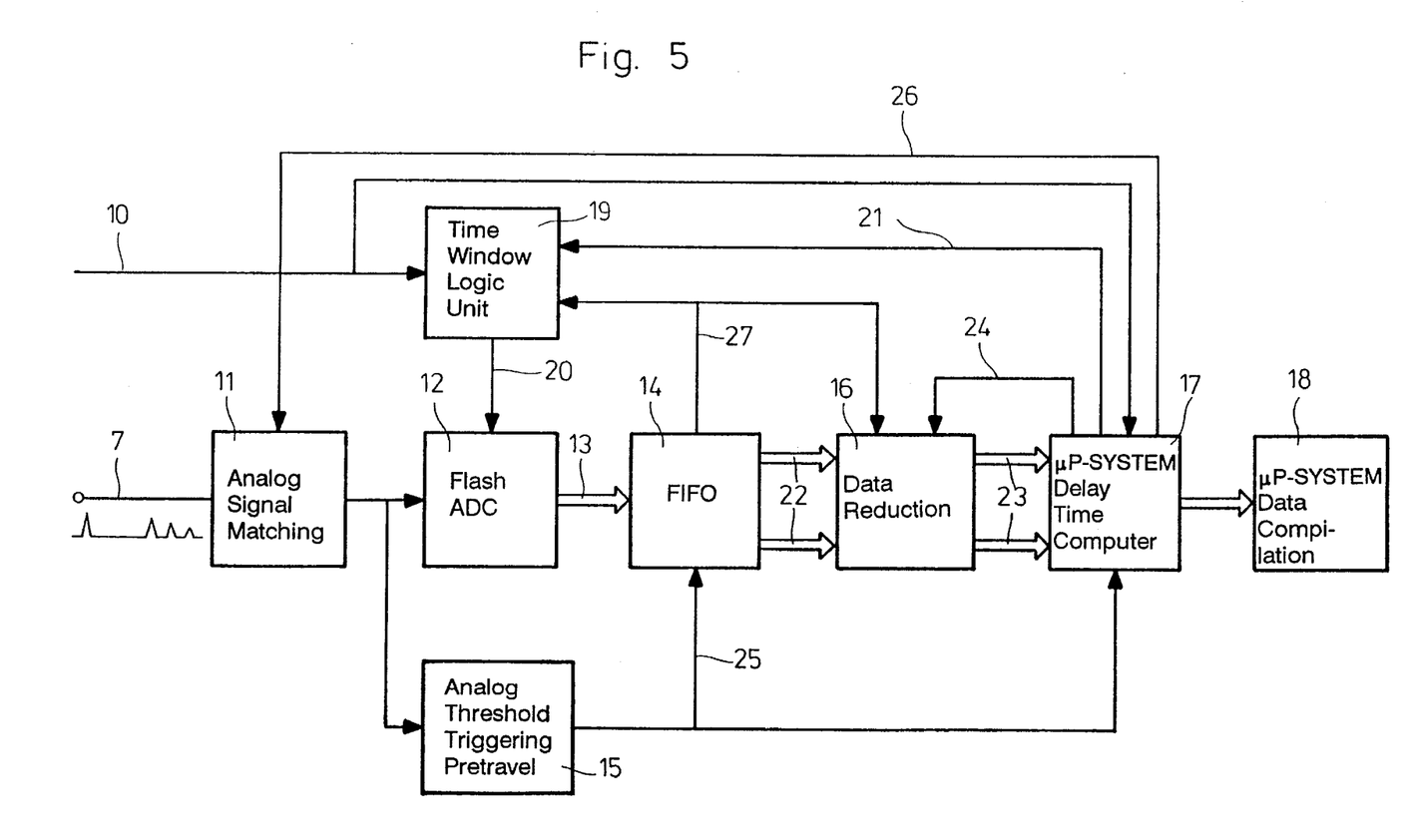
FIG. 5 is a block circuit diagram for an arrangement for implementing the method according to the invention.

The processing of an echo signal will now be described with reference to the block circuit diagram of FIG. 5.

An echo signal 7 is initially rectified and smoothed in 11 and then fed to an A/D converter 12 which digitizes the signal with a resolution of 8 bits. The corrosion measurement is usually performed with sensors that have a resonant frequency of 5 MHz. In order to unequivocally detect peak amplitudes, the A/D conversion is effected at a sampling rate of 28 MHz. The digital amplitude values 13 are then stored in an intermediate FIFO memory 14. Depending on the wall thickness to be tested, the memory depth is 256 or 512 bytes, respectively, which corresponds to a data detection period of 9 and 18 µs, respectively. The digitalization is therefore limited to only the pulse sequence of front wall echo and subsequent rear wall echoes.

Figure 6A:
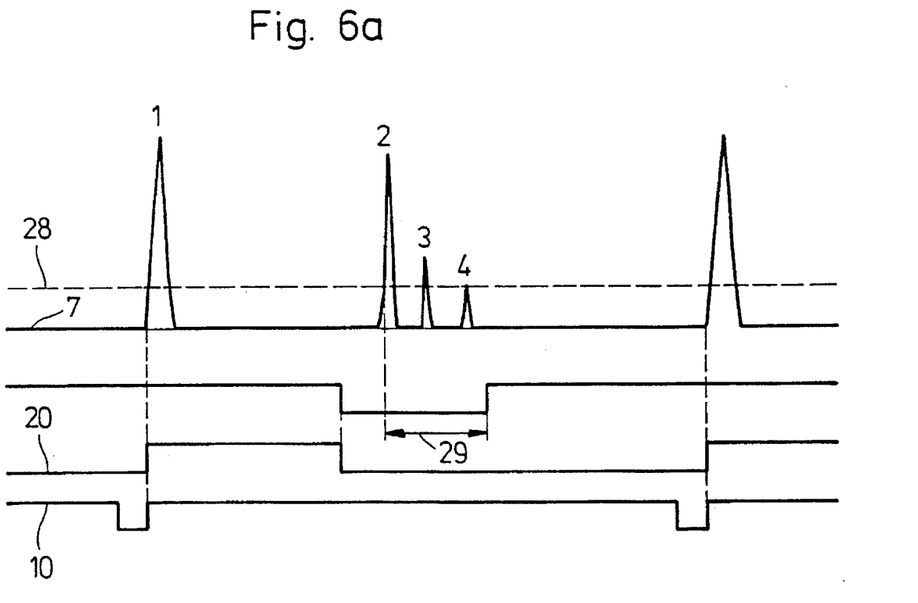
FIGS. 6a, 6b, 7a and 7b depict signal processing results for two different ultrasound pulses.
Figure 6B:
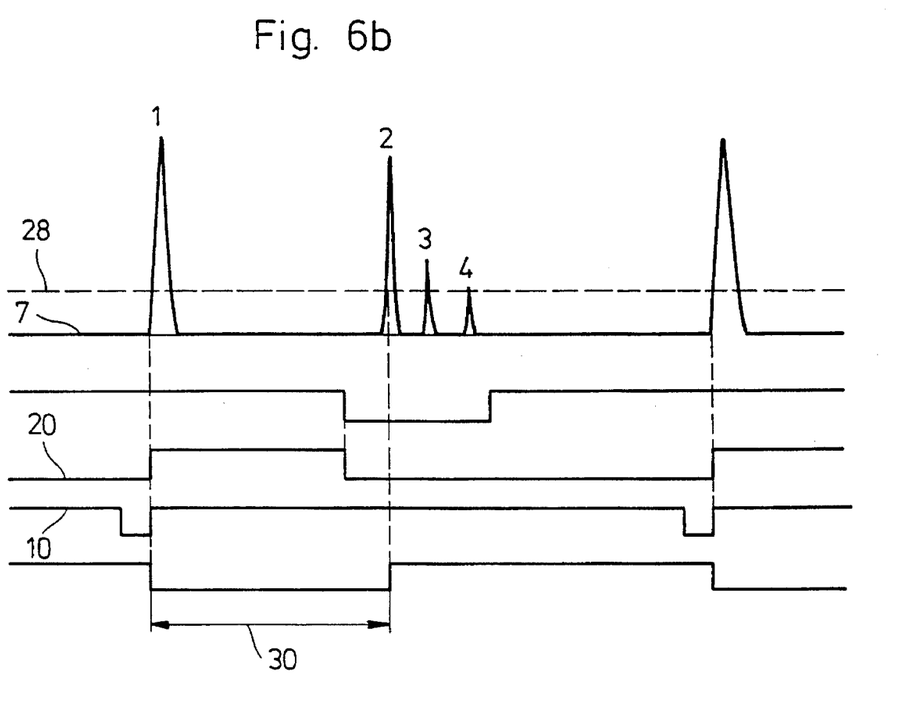

The determination of the lead time is made in the conventional manner with the aid of a clocked counter that is started by the start-of-transmission pulse (SAP) 10 and is stopped again by inner wall echo pulse 2 when the predetermined triggering threshold is exceeded in 15. The lead path thus corresponds to the time difference 30 between transmitted pulse 1 and front wall echo pulse 2—FIG. 6b.

The A/D conversion is initiated at the end of a variable time window ("start ADC") 20. This variable time window may be generated by a separate hardware circuit 19 or by the delay time computer 17, 21. If the time aperture is generated by the delay time computer 17, changes in the sensor distance from the interior wall of the pipe, which may be caused, for example, by sensor carrier deformation, can be compensated. Thus it is always possible to generate an optimum conversion window. The generation of the time aperture is configured as a self-learning system. In order to detect the entire echo pulse sequence, the width of the aperture must be set in such a way that it will not exceed the shortest lead time to be expected.

As soon as the front wall echo 2 exceeds the lead triggering threshold 28 and thus stops the counter, the data stored up to this point in time are erased 25, and 256 or 512 new values, respectively are read in at 29. Thus optimum utilization of the existing memory capacity is ensured for sufficiently strong echo signals. Data compilation 29 then begins immediately upon the arrival of front wall echo 2 and includes, in addition to the first rear wall echo, subsequent echoes 4 generated by multiple reflections, FIG. 6a.

Figure 7A:
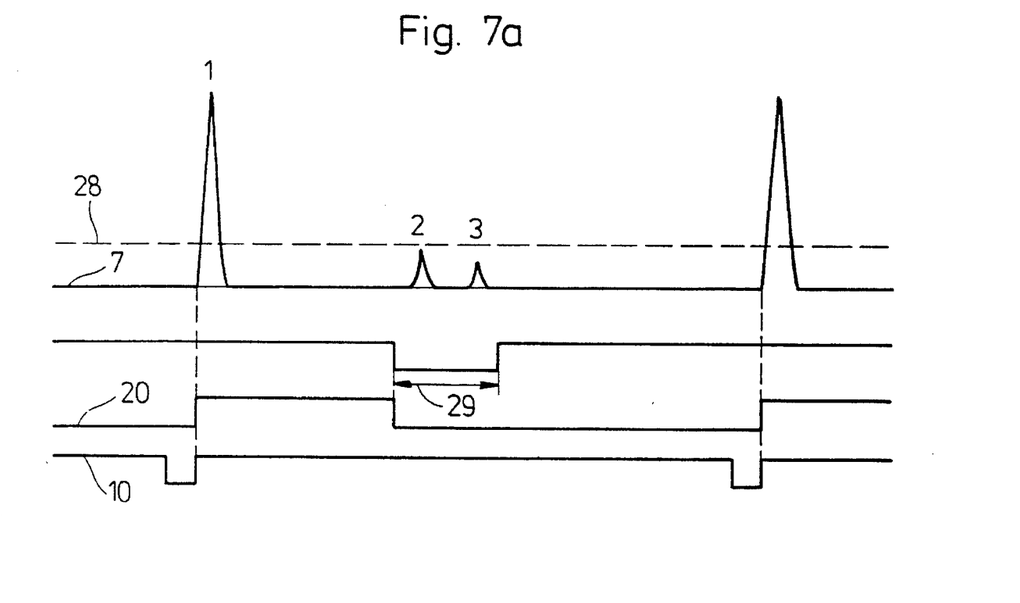
Figure 7B:
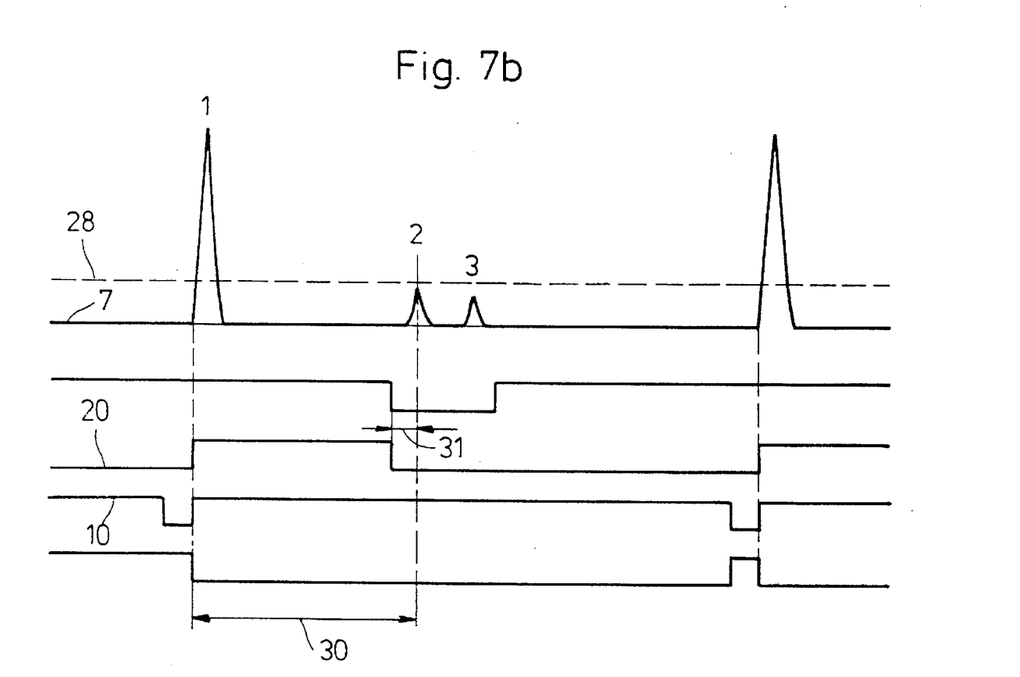

If echo signal 7 remains below triggering threshold 28, then the FIFO memory 14 is not erased and digitalization stops after a period 29 of 9 or 18 μs, respectively (FIG. 7a). In this case, the subsequent digital signal evaluation is limited essentially to a determination of the pretravel path. If there is no lead triggering, the lead time 30 is calculated as the sum of the width of the "start ADC" aperture 20 and the time association of the first stored echo pulse 31 (FIG. 7b).

Due to the quantity of data which, depending on the sampling time, lies above the data quantity of the prior art data recording system (one byte for the pretravel path and one byte for the wall thickness per sounding) by a factor of 128 and 256, respectively, a digital on-line calculation of the delay time must be performed.

If the echoes are sounded at a rate of 400 Hz, the time interval between two transmitted pulses for 64 sequentially approached sensors is 39 μs. However, it is not possible with the aid of a microprocessor to run an algorithm that must process up to 512 data values in 39 μs for the delay time determination. Therefore, before the digitized values 22 are transferred to the processor, a data reduction must be performed.

This data reduction 16 can be realized only by fast hardware. The reduced data set 23 must here retain all informations of the original pulse sequence which are relevant for a determination of the delay time. Of interest are the position of the pulses, their maximum amplitudes and the shape of the pulses.

Additionally, only those pulses are considered which exceed a preselected digital threshold.

Figure 8A:
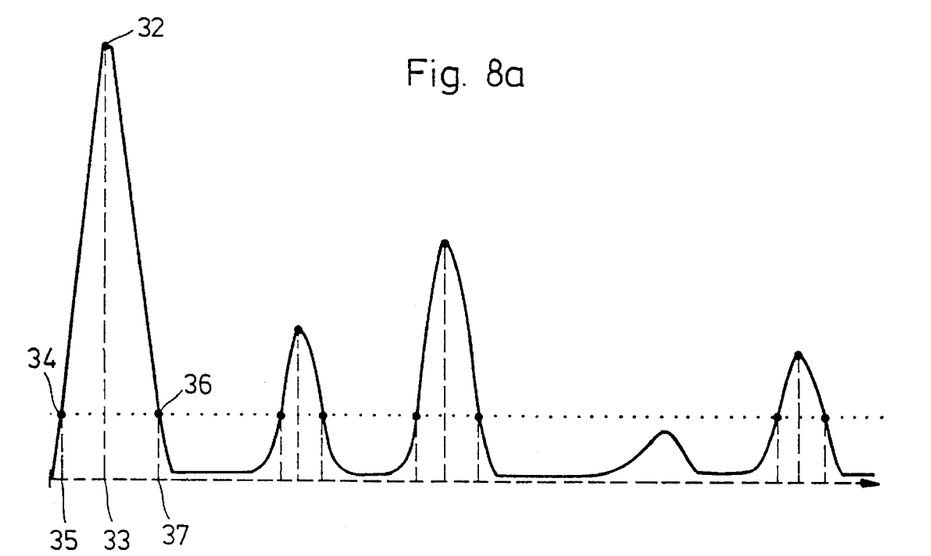
FIGS. 8a, 8b and 8c depict exemplary data reductions.

For this purpose, the digitized amplitude values are read out of the intermediate FIFO memory 14 and compared with the digital threshold 24. If the signal amplitude lies below the threshold value, the digitized value is selected. If the signal exceeds the threshold value, this value 34 and its time association 35 are transferred to the evaluation computer; the subsequent values until the amplitude maximum appears are again filtered out. The amplitude maximum 32 and its time association 33 are stored; also stored is the subsequent time value 37 at which the threshold 36 is not reached or fallen below (FIG. 8a).

The digital threshold value may be preset by way of the hardware or may be generated by the delay time computer 24. If generated by the delay time computer, the threshold value may adapt itself in a self-learning manner to roughnesses in the walls and the sensor characteristics. The criterion for changing the threshold value is the number of pulses that exceed the threshold value.

Figure 8B:
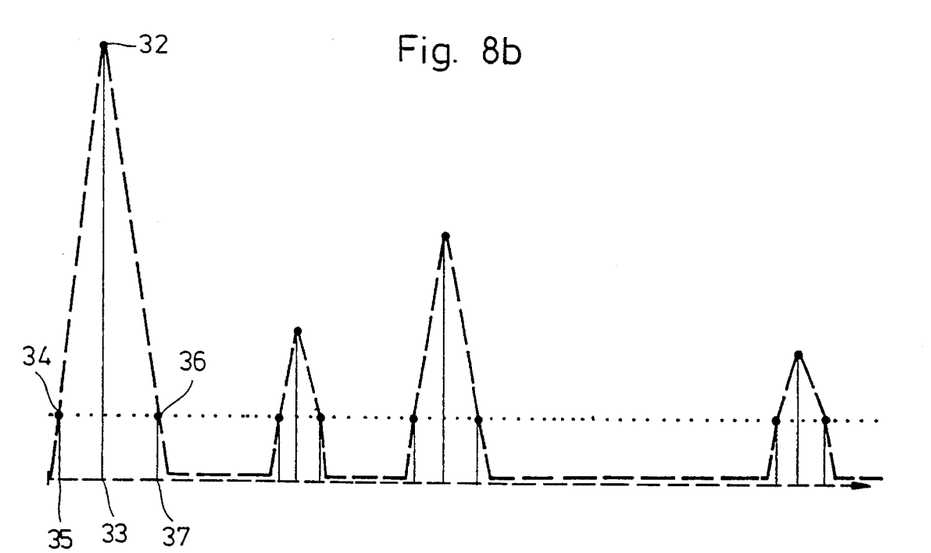

If, in addition to the pulse peaks, the amplitude and time values upon exceeding (34, 35) or not reaching (36, 37) the digital threshold value are stored, it is possible to obtain information about the shape, that is, the width of the echo pulses. The original echo pattern can thus be recorded in a memory space saving manner and can be reconstructed almost completely with the aid of these reduced data sets (FIG. 8b).

Figure 8C:
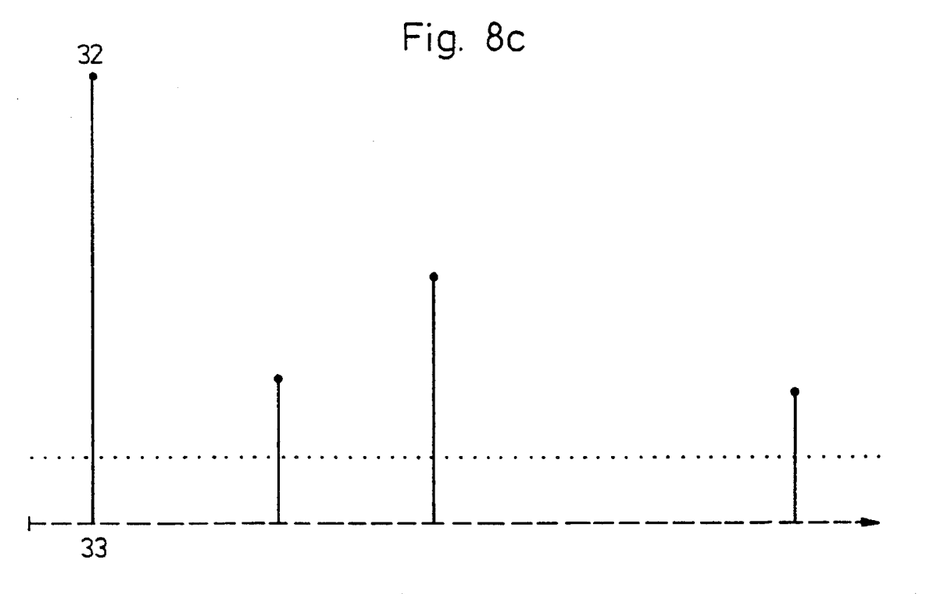

Depending on the power of the available microprocessor, it may be necessary to further reduce the data. In that case, only the height 32 of the pulses and their time association 33 are transferred to the evaluation computer; the original set of data is thus reduced to the pulse maxima (FIG. 8c).

The ultrasound echo signal from individual sensors may be attenuated by external influences in such a way that the reflected pulses lie below the minimum triggering threshold. Only an individual gain adaptation 26 as a function of the attenuation then permits a measurement of the delay time.

A measure for the gain adaptation are the maximum amplitudes of the reflected pulses as determined over a predetermined number of excitation pulses. Individual outliers are not considered.

After the reduced data sets are transferred, the tasks of the microprocessor system are the following:

- to filter out the echo pulses that are relevant for a determination of the delay time;
- to determine the delay time of the echo signal in the pipe wall on the basis of the time intervals between pulse peaks;
- to check the validity of the obtained results;
- to determine the pretravel with the aid of the internal counter or, if no lead triggering took place, calculate it.

If the surface is rough, several front wall pulses may be received. From several front wall pulses that must lie within a defined time frame the microprocessor selects the pulse with the highest amplitude. Thus, it is possible to correct the front wall delay time.

If there is heavy corrosion it may happen that the algorithm based on physical laws and empirical values is unable to perform an unequivocal delay time measurement. In that case, the entire reduced echo pattern is stored in a memory. Upon completion of the test run, the delay time can then be determined manually.

Since the delay time must be determined on-line, it is necessary, because of the limited computing time available, to optimize the evaluation algorithm with respect to the error situations occurring most frequently.

Figure 9A:
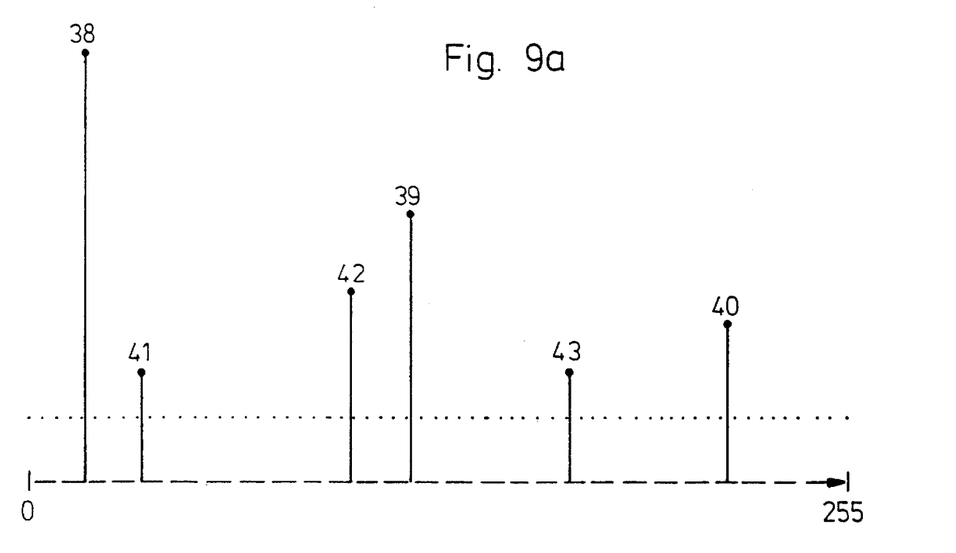
FIG. 9 depicts the selection of relevant data.
Figure 9B:
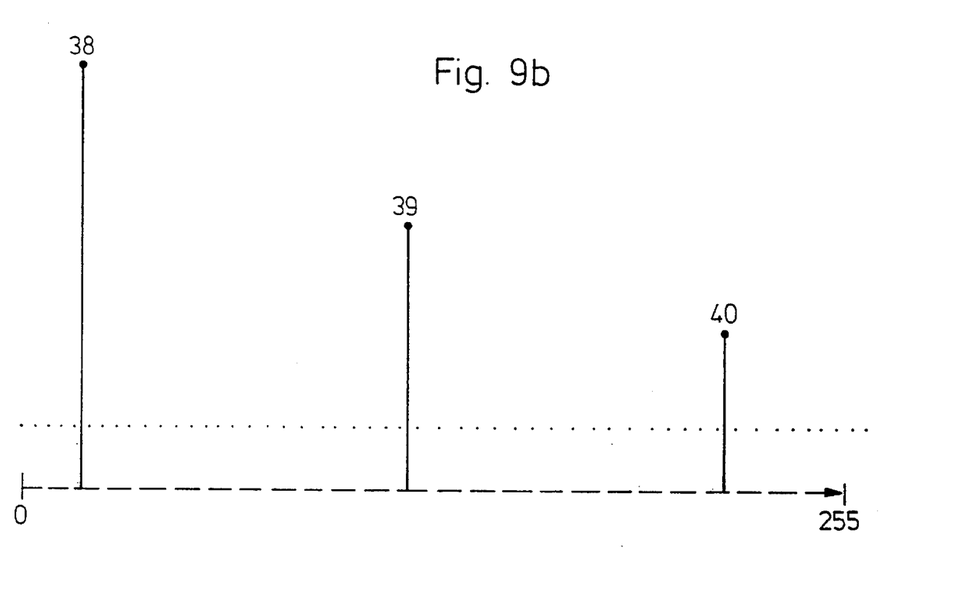

After reading in the reduced data 23 (amplitudes and time association of the pulse peaks), FIG. 9a, the pulses relevant for a determination of the delay time must initially be sorted out. In this connection it is assumed that the pulse sequence including (the front wall echo, the first rear wall echo, the second rear wall echo, . . .) has monotonously decreasing amplitudes 38, 39, 40. Lower amplitude echo pulses lying therebetween are considered to be interference signals 41, 42, 43. For this purpose, the pulses are checked from the back towards the front with respect to time, i.e., from pulse 40 toward pulse 38: an echo pulse is considered to be relevant and is stored if its amplitude is greater than or almost equal to the amplitude of the last stored pulse, FIG. 9b.

Then the thus filtered pulse sequence is examined with the aid of the most frequently occurring echo pattern variations and the delay time for the ultrasonic signal in the pipe wall is determined. The result is then compared with the momentary reference value, that is, with a value to be expected.

A measured value is considered to be particularly reliable if the distance in time between the entrance echo and the first rear wall echo coincides with the distance between the first and the second rear wall echo. This value is then considered to be the new reference value. The expectancy range for the next wall thickness value to be determined results from the last wall thickness value, that is, the reference value +/− a tolerance range that is a function of the wall thickness.

The tolerance range adapts itself to changing wall thicknesses in a self-learning manner.

The conventional delay time measuring method operating according to the pulse reflection method in connection with wall thickness measurements is limited to merely the front wall echo and the first rear wall echo. Due to the more difficult conditions under which corrosion tests in pipelines are performed, this method frequently leads to error measurements or missing measuring values. A significant improvement in the signal evaluation is realized in the method according to the invention in that the entire echo signal pattern, that is, the front wall echo, the first rear wall echo and the subsequent rear wall echoes caused by multiple reflections are included in the consideration and are evaluated with the aid of a microprocessor system.

This initially requires the digitalization of the echo signal and, since the evaluation must be made on-line, reduction of the data with the aid of a fast hardware system.

In addition to a determination of the delay times, the use of the microprocessor system permits monitoring of the signal amplitudes and thus control of the signal gain. Additionally, the position of the time window for recording the echo pulse sequences can be optimally adapted to the signal pattern.

If, due to heavy corrosion, it should not be possible to make an unequivocal delay time determination on-line, the entire reduced echo pattern is stored. A more extensive evaluation of the echo pattern can thus be performed after the test run is completed.

List of Reference Numerals

| | |
|---|---|
| 1 | transmitted ultrasound pulses |
| 2 | front wall echo pulse |
| 3 | first rear wall echo pulse |
| 4 | second rear wall echo pulse |
| 5 | third rear wall echo pulse |
| 6 | fourth rear wall echo pulse |
| 7 | ultrasound echo signal |
| 8 | measuring gate for wall thickness |
| 9 | measurement blocking aperture |
| 10 | transmission initiation pulse SAP |
| 11 | amplifier/filter module |
| 12 | analog/digital converter |
| 13 | digitized amplitude values |
| 14 | intermediate FIFO memory |
| 15 | analog threshold value triggering for a determination of the lead time |
| 16 | data reduction |
| 17 | µP system delay time computer |
| 18 | µP system data compilation |
| 19 | time window logic unit |
| 20 | control signal "start ADC" |
| 21 | control line "set time window" |
| 22 | value pairs (amplitude, time association) |
| 23 | reduced data (amplitude, time association) |
| 24 | digital threshold value (data reduction) |
| 25 | reset line (erasing the FIFO) |
| 26 | control line "gain control" |
| 27 | control line "FIFO full" |
| 28 | analog triggering threshold (lead determination) |
| 29 | data compilation period |
| 30 | lead time |
| 31 | time association of the first stored echo pulse |
| 32 | amplitude of the pulse maximum |
| 33 | time association of the pulse maximum |
| 34 | amplitude when the digital threshold is exceeded |
| 35 | time association when the threshold value is exceeded |
| 36 | amplitude when the digital threshold is not reached |
| 37 | time association when the digital threshold is not reached |
| 38, 39, 40 | relevant echo pulses |
| 41, 42, 43 | interference pulses |

We claim:

1. A delay time measuring method for ultrasound employing the pulse reflection method, wherein at least one excitation pulse that is as close as possible to the shape of a shock wave is emitted by a testing head and traverses a pretravel path until the excitation pulse reaches an object to be examined which has a front wall and a rear wall, with at least one reflected echo pulse being generated at the front wall of the object and at least two reflecting echo pulses being generated at the rear wall of the object, and wherein the reflected echo pulses are detected by at least one ultrasound detector and are amplified by analog signal matching, and wherein:

(a) a time window is set for receiving the reflected echo pulses following the excitation pulse, with the width of said window being such that the front wall echo pulse and at least the two rear wall echo pulses lie within the window, and said received reflected echo pulses are digitized; then (b) the reflected echo pulses lying within the time window are digitally filtered and parametrized, wherein for each one of said reflected echo pulse lying within the time window, the time and amplitude are detected for the maximum and for when a digital threshold value is exceeded and fallen below; whereupon (c) the times and amplitudes of the filtered and parametrized reflected echo pulses are fed to a computer unit, wherein the parametrized reflected echo pulses are checked with respect to time from the most recently received rear wall echo pulse to the front wall echo pulse, and the parameterized reflected echo pulse being checked is considered to be relevant and is stored when the amplitude of the echo pulse being checked is nearly identical to or greater than the amplitude of the most recently stored echo pulse; and finally (d) the lead time and the wall thickness delay time of the object are determined and stored when the distance in time between the front wall echo pulse and the first rear wall echo pulse coincides with the distance between the first and second rear wall echo pulses within a tolerance band, and the times and amplitudes of all filtered and parametrized reflected echo pulses belonging to said one excitation pulse are stored when the distance in time between the front wall echo pulse and the first rear wall echo pulse does not coincide with the distance between the first and second rear wall echo pulses within the tolerance band.

2. The method according to claim 1, wherein the time window is optimized in a self-learning manner to the pattern of the reflected echo pulses.

3. The method according to claim 1, wherein the digitization of the reflected echo pulses employs high sampling rates, and the data are intermediately stored in a fast memory before being subjected to filtering.

4. The method according to claim 2, wherein the digitization of the reflected echo pulses employs high sampling rates, and the data are intermediately stored in a fast memory before being subjected to filtering.

* * * * *